United States Patent [19]
Bessler et al.

[11] Patent Number: 5,549,621
[45] Date of Patent: Aug. 27, 1996

[54] APPARATUS AND METHOD FOR PERFORMING VERTICAL BANDED GASTROPLASTY

[75] Inventors: Marc Bessler, Teaneck, N.J.; Max R. Mintz, Houston, Tex.; Byron C. Sutherland, 2458 Country Club Dr., Pearland, Tex. 77581

[73] Assignees: Byron C. Sutherland; Hava Mattea Mintz; Conley, Rose & Tayon, P.C., all of Houston, Tex.

[21] Appl. No.: 399,958

[22] Filed: Mar. 6, 1995

Related U.S. Application Data

[63] Continuation of Ser. No. 62,205, May 14, 1993, abandoned.

[51] Int. Cl.$^6$ ............................................... A61B 17/00
[52] U.S. Cl. ........................... 606/151; 606/139; 606/157; 227/902
[58] Field of Search ......................... 606/139, 142, 606/151, 157, 158, 205, 207, 213, 219–221, 215; 227/902; 128/898, 899

[56] References Cited

U.S. PATENT DOCUMENTS

| | | | |
|---|---|---|---|
| 3,357,296 | 12/1967 | Lefever | 606/220 |
| 3,687,131 | 8/1972 | Rayport et al. | 606/157 |
| 4,487,205 | 12/1984 | Di Giovanni et al. | 606/158 |
| 4,519,392 | 5/1985 | Lingua | 606/157 |
| 4,558,699 | 12/1985 | Bashour | 606/157 |
| 4,754,758 | 7/1988 | Li | 606/213 |
| 4,827,930 | 5/1989 | Kees, Jr. | 606/142 |
| 4,844,068 | 7/1989 | Arata et al. | 606/205 |
| 4,930,502 | 6/1990 | Chen | 606/151 |
| 4,944,741 | 7/1990 | Hasson | 606/207 |
| 5,040,715 | 8/1991 | Green et al. | 227/176 |
| 5,104,394 | 4/1992 | Knoepfler | 606/143 |
| 5,170,925 | 12/1992 | Madden et al. | 227/175 |
| 5,171,258 | 12/1992 | Bales et al. | 606/205 |
| 5,188,636 | 2/1993 | Fedotov | 606/151 |
| 5,222,963 | 6/1993 | Brinkerhoff et al. | 606/220 |
| 5,234,443 | 8/1993 | Phan et al. | 606/148 |
| 5,258,011 | 11/1993 | Drews | 606/220 |

FOREIGN PATENT DOCUMENTS

| | | | |
|---|---|---|---|
| 1410958 | 7/1988 | U.S.S.R. | 606/144 |
| 1574215 | 6/1990 | U.S.S.R. | 606/157 |

*Primary Examiner*—Gary Jackson
*Assistant Examiner*—Jeffrey A. Schmidt
*Attorney, Agent, or Firm*—Conley, Rose & Tayon, P.C.

[57] ABSTRACT

The present invention pertains to an apparatus and method which enable the performance of vertical banded gastroplasty (VBG) without the use of staples. Further, a laparoscopic instrument which can be used in combination with the VBG apparatus and method is also disclosed.

The laparoscopic instrument can also be used in combination with surgically functional elements other than the VBG apparatus. A particular advantage of the laparoscopic instrument is that surgically functional elements attached at the leading edge of levered jaws of the instrument can be rotated at least 180 degrees in a plane which is substantially parallel to a plane passing horizontally through the longitudinal centerline of the levered jaws.

18 Claims, 8 Drawing Sheets

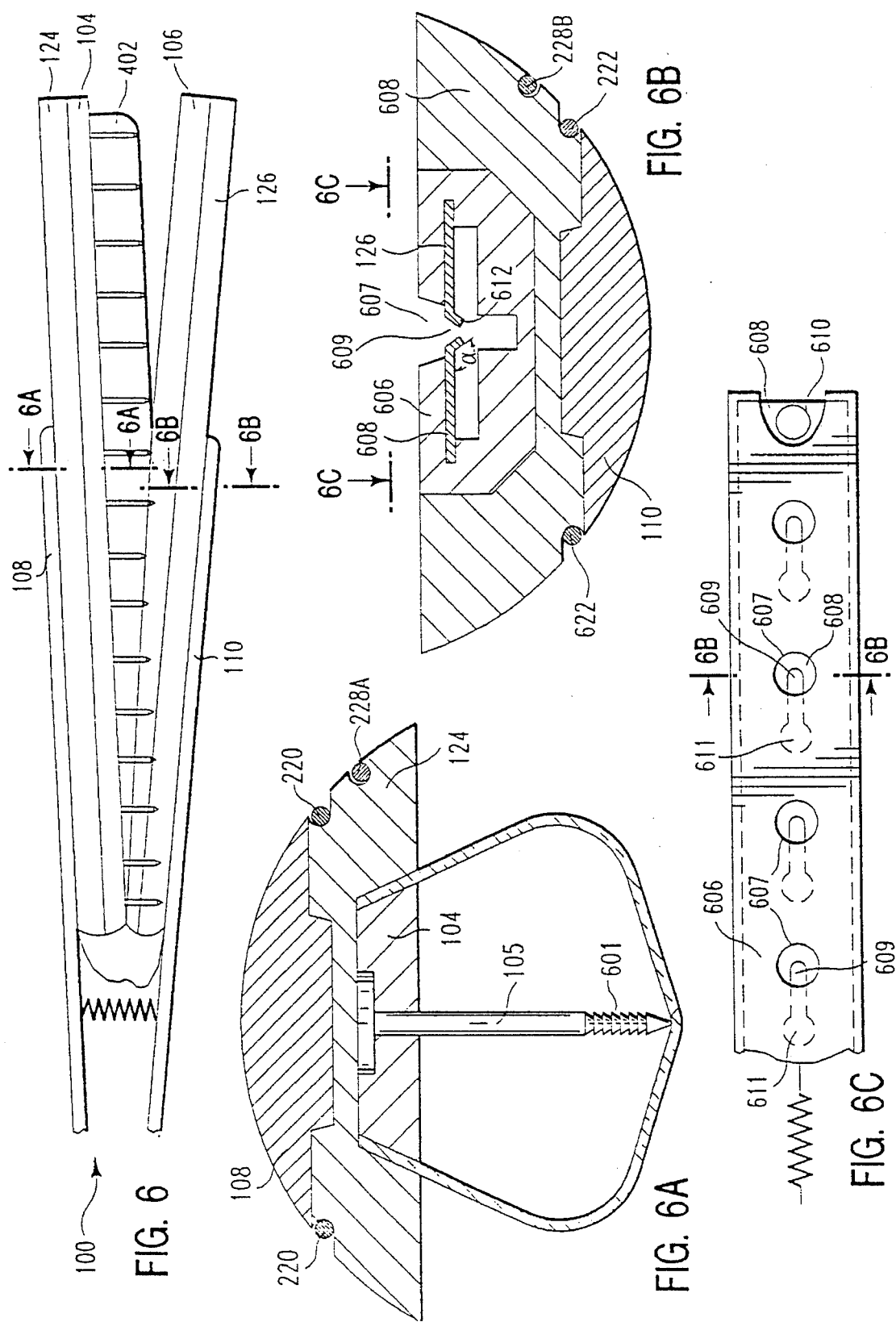

APPARATUS AND METHOD FOR PERFORMING VERTICAL BANDED GASTROPLASTY

This is a continuation of application Ser. No. 08/062,205 filed on May 14, 1993 now abandoned.

BACKGROUND OF THE INVENTION

1. Field of the Invention

The present invention pertains to an apparatus and method which enable vertical banded gastroplasty to be performed without the use of staples, and preferably laparoscopically.

2. Description of the Background Art

Morbid obesity is a significant health problem in the United States, affecting over four million people. Morbid obesity occurs when the obesity is sufficient to prevent normal activity or physiologic function, or is sufficient to cause onset of a pathologic condition. (Morbid obesity is strictly defined as 80 lbs or more overweight for women and 100 lbs or more overweight for men). People who are morbidly obese are more than ten times as likely to die each year as normal age matched controls. The death rate for patients with morbid obesity is about 2.5% per year. In addition to the health risks, the socioeconomic and psychological effects of morbid obesity are significant. The only known effective long term therapy for morbid obesity is surgical, since dieting may allow the morbidly obese to lose weight but this loss is almost always temporary.

Several surgical procedures are available for treatment of morbid obesity, but the most commonly performed is Vertical Banded Gastroplasty (VBG). In VBG, an upper gastric pouch is formed within the stomach, using the stomach walls for the reconstruction. The upper pouch is formed using a vertical staple line, with a band (typically Silastic® or Marlex®) applied to prevent dilation of the outlet from the upper pouch into the remaining portion of the stomach. Since bodily sensors which cause a person to feel "full" are located in the area in which this upper gastric pouch is formed, as the upper pouch stretches to contact the sensors, the person tends to stop eating. VBG has a mortality rate of about 0.5% and is effective in long term (a period of 5 years or more) weight loss for the majority of patients. The statistically small, but significant, risks of VBG have been more than outweighed by the decreased mortality rate of morbidly obese persons after surgery. However, it is standard practice of physicians to restrict the VBG procedure to persons who are morbidly obese, due to the statistically significant risks involved.

A large portion of the morbidity attributed to VBG is related to respiratory and wound complications in this medically at risk population. It would be, then, highly desirable to have a laparoscopic procedure to accomplish VBG in order to reduce wound complications, pain, recovery time, and length of bed rest related to the surgery. Advantages of the laparoscopic procedure should include faster recovery, decreased respiratory and wound complications, decreased post-operative pain and decreased scarring.

One of the more significant barriers to performance of a laparoscopic VBG has been the absence of an adequate stapling device for use under laparoscopic conditions. A 90 mm stapler having a straight line construction design is generally used in the open surgical procedure. A stapler of this dimension and design could not be used in laparoscopic surgery in which the diameter of the opening ports into which surgical instruments are inserted ranges from about 5 mm to about 35 mm.

U.S. Pat. No. 5,170,925 to Madden et al., issued Dec. 15, 1992, discloses a laparoscopic stapler with knife means. A four-row laparoscopic surgical stapler cutting mechanism is described wherein stapling and cutting are remotely accomplished. Particular means which enable closure and stapling of the apparatus are described. Closure of the apparatus can take place either using a lever or a collar type means. Another automatic stapler for laparoscopic procedure is disclosed in U.S. Pat. No. 5,104,394 to Knoepfler, issued Apr. 14, 1992. In particular, this patent describes an improved surgical stapler which includes a cutter adapted to cut items grasped by the stapler jaws and a suctioning tube at the tip of the apparatus. This improved stapler permits a surgeon to staple and subsequently selectively cut without removing the apparatus. Still another apparatus for placing staples in laparoscopic or endoscopic procedures in described in U.S. Pat. No. 5,040,715 to Green et al., issued Aug. 20, 1991. This patent describes a surgical stapler for placing lateral lines of staples and making an incision, all through an endoscopic tube.

Although the development of such stapling devices permits laparoscopic placement of staple lines, they do not provide for the placement of a 90 mm staple line nor for placement of the band at the outlet of the pouch formed by the stapling of the stomach walls.

Conventional VBG requires that a circular hole be made in the stomach to allow for placement of the vertical staple line and horizontal band. This circular hole is usually accomplished using a stapling/cutting device that removes a circular portion of stomach and places several circular rows of staples. This configuration of staple placement is difficult to perform laparoscopically and makes it more difficult to reverse the procedure should this be necessary. Thus, it would be desirable to have a device and method which would permit performance of VBG without the use of a circular opening and staple configuration.

Further, patient experience has demonstrated numerous incidents pertaining to VBG, by any surgical procedure, wherein staples have become detached from the stomach, causing a gradual opening of the pouch into the entire stomach.

Thus, it would be desirable to have an alternative to the stapling procedure for formation of the upper gastric pouch. Even more desirable would be an alternative procedure wherein the band at the outlet of the pouch was formed simultaneously with the pouch. Such an alternative procedure performed laparoscopically might enable reduction of the mortality rate for VBG to a level such that the procedure could be made available to individuals who do not fall into the morbidly obese category, but who have a sufficiently significant overweight condition that their health is adversely affected.

SUMMARY OF THE INVENTION

In accordance with the present invention, an apparatus and method which enable vertical banded gastroplasty (VBG) to be performed without the use of staples are disclosed. Further, a laparoscopic instrument which can be used in combination with various devices for permitting different kinds of laparoscopic surgery is also disclosed. This laparoscopic instrument can be used in combination with the apparatus and method for enabling VBG.

The apparatus of the present invention which pertains to VBG is a pouch-forming device which remains in the body of the patient after surgery. The pouch-forming device is comprised of at least two clamping bars designed to act in conjunction with each other and preferably having at least one banding strip attached to corresponding ends of each of the clamping bars. This combination of clamping bars and banding strip is applied to the stomach in a manner so that an upper gastric pouch is formed using the walls of the stomach. The clamping bars are applied with one bar anterior and one bar posterior to the exterior of the stomach so that when the bars are "clamped" together, a tubular-shaped (initially) pouch is formed. The upper ends of the clamping bars are located at the junction of the esophagus with the stomach. The lower ends of the clamping bars form the base of the initially tubular-shaped pouch and are attached to the banding strip which forms a confined, banded opening from the base of the pouch. The banded opening is located away from the junction of the esophagus with the stomach, so that the clamping bars tend to be somewhat vertical relative to the upper and lower openings from the stomach, thus, the terminology "VBG" applies.

The clamping bars typically have tissue piercing pins which protrude from a first clamping bar with a pin-receiving openings and a pin locking mechanism in the corresponding, second clamping bar. The pin length is designed to permit the stomach tissue held between the first and second clamping bars, and pierced by the pins to receive normal sustenance and to heal around the pins, so that minimal alteration of the stomach tissue occurs due to the presence of the clamping bars. A particular advantage of this apparatus over stapling is that stress exerted upon the exterior of the stomach wall tends to be distributed over the entire stomach surface in contact with the clamping bar, rather than singly at the point at which the stomach is pierced (in contrast with staples). Further, the clamping bar containing the piercing pins is designed so that the entire bar must be released from the stomach to have there be a danger of a sharp point contacting other internal tissues (in contrast with individual staples which can tear loose). And finally, when clamping bars are used which have a band attached at corresponding ends, the pouch formation and banding at the base of the pouch are accomplished in one operation by application of the apparatus of the present invention to the stomach.

Although the pouch-forming device and its method of application to the stomach were originally designed for use in combination with a laparoscopic instrument, the device and method can also be used to form an upper gastric pouch during standard open surgery VBG. In the case of open surgery, the dimensions of the pouch-forming device can vary, since the device need not fit within the confines of the laparoscopic instrument. However, the pouch-forming device operates to form an upper gastric pouch in the manner described above.

Further, in accordance with the present invention, an apparatus useful in performing laparoscopic surgery is provided. This apparatus permits the rotation, over at least 90 degrees, of surgically functional elements of the apparatus.

In one preferred embodiment of the present invention, the laparoscopic instrument includes:

a) a tubular length used to enclose surgically functional elements at the time the instrument is inserted through a port into a body cavity;

b) at least one arm which can be extended from and retracted into the tubular length;

c) a rotatable holder attached to the at least one lever arm at the leading end of the lever arm (leading end with reference to entering the body); and d) at least one surgically functional element capable of performing a desired surgical function, wherein the surgically functional element is attached to the rotatable holder.

In the case of VBG, there are at least two arms, used as lever arms, wherein each lever arm is attached to a rotating clamping bar. The clamping bar holder is attached to a clamping bar used as part of a pouch-forming device. The rotational holder is capable of rotating at least 90 degrees, and preferably at least 180 degrees, in a plane which is relatively parallel to a horizontal plane passing through the longitudinal centerline of the lever arm attached to the rotational holder. The trailing end of each lever arm is attached to a pivot which joins the lever arms together and upon which the lever arms open and close relative to each other. The pivot is further attached to a rod or tubular insert which can be used to hold the lever arms in position relative to the interior surface of the tubular length used to enclose the surgically functional elements of the laparoscopic instrument. The tubular length, the first tubular structure, contains the lever arms during insertion of the laparoscopic instrument through an insertion port into patient's body. A second tubular structure surrounds the first tubular structure in a manner providing a snug but slidable fit, so that when the first tubular structure is fully extended, the lever arms, rotatable holders, and surgically functional elements are enclosed within the first tubular structure. As the first tubular structure is retracted into the second tubular structure, the surgical functional elements, their rotatable holder's, and at least a portion of the lever arms become exposed. Simultaneously with exposure of the lever arms, as the first tubular structure is retracted, the lever arms open under an applied force (such as a spring) which tends increase the included angle between them at the pivot which holds the lever arms together. The first tubular structure is typically connected to a means which enables the extension and retraction of the first tubular structure.

In a second preferred embodiment, the laparoscopic instrument includes:

a) at least one arm;

b) a rotatable holder attached to the at least one lever arm at the leading end of the arm; and c) at least one surgically functional element capable of performing a desired surgical function, wherein the surgically functional element is attached to the rotatable holder.

In the case of VBG there are at least two arms, used as lever arms, wherein a pivot joins the lever arms together near the trailing end of each lever arm. The lever arms are in a normally open position (have a large included angle between them) due to the action of an applied force. The trailing end of at least one of the lever arms is in the form of a first ramp. This first ramp operates in complimentary fashion with a second ramp on the leading end of a push rod. The push rod can be used to force the lever arms into a closed position. The push rod is enclosed in a tubular structure which is attached to or adjacent the lever arms.

In each of the preferred embodiments described above, cables are present adjacent the rotatable holders and are attached to a means for rotating the rotatable holders at the leading edge of the lever arms. These cables are preferably controlled using a knob located on a handle means of the laparoscopic instrument to which at least one of the tubular structures previously described are attached.

In each of the preferred embodiments described above, in addition to the cables used to rotate the rotatable holders, at least one additional cable is present at a position adjacent the rotatable holders; the cable is connected to a release means which permits release of the element(s) capable of performing the desired surgical function. (In the case of VBG, additional cables permit separation of the clamping bars from their holders).

The laparoscopic instrument of the present invention preferably includes additional means for avoiding potential harm to a patient should a surgeon perform a first critical step which must then be followed by a second critical step, but become distracted prior to performing the second critical step. Such a safety means is typically a mechanism which permits execution of the next step in a series of steps only after a specific step has been completed. (In the case of VBG, damage to the patient's stomach could occur, should the surgeon become temporarily distracted and attempt to remove the clamping bars after they have been engaged but before releasing the clamping bars from their holders.) To prevent this from occurring, a preferred embodiment of the VBG laparoscopic instrument of the present invention functions so that once the clamping bars are engaged, they are automatically released from their rotatable holders. Further, a safety means for preventing unintentional closing of the lever arms is highly recommended.

The method of using the VBG laparoscopic instrument of the present invention in combination with the pouch forming device of the present invention includes the following steps:

a) inserting gastric pouch-forming clamps mounted on rotatable clamp holders which are attached to lever arms, through a pre-prepared port into the abdominal cavity of a patient;

b) rotating the clamp holders so that the pouch-forming clamps are placed in the desired position relative to the stomach, with at least one clamp on the exterior anterior side of the stomach and at least one clamp on the exterior posterior side of the stomach;

c) engaging the pouch-forming clamps so they cooperate to form an upper gastric pouch;

d) releasing the pouch-forming clamps from their clamp holders;

e) rotating the clamp holders so they are in a parallel position relative to said lever arms; and f) removing the portion of the laparoscopic instrument other than the clamping apparatus from the abdominal cavity of the patient.

Step e) above may be followed by a step $e_2$) wherein the clamp holders are retracted into a laparoscopic instrument tubular structure, depending on the structure of the instrument.

Additional steps which may precede step a) above include:

$a_2$) attaching a pouch-forming clamp to a rotatable clamp holder of a laparoscopic instrument;

$a_3$) aligning the pouch-forming clamp, and rotatable clamp holder relative to a lever arm of the laparoscopic instrument;

BRIEF DESCRIPTION OF THE DRAWINGS

FIG. 6 is a schematic of a second preferred embodiment of the clamping apparatus.

FIG. 6A is a cross-sectional view taken along lines 6A—6A of FIG. 6.

FIG. 6B is a cross-sectional view taken along lines 6B—6B of FIG. 6.

FIG. 6C is a plan view taken along lines 6C—6C of FIG. 6B.

DETAILED DESCRIPTION OF THE PREFERRED EMBODIMENTS

Figure 1:
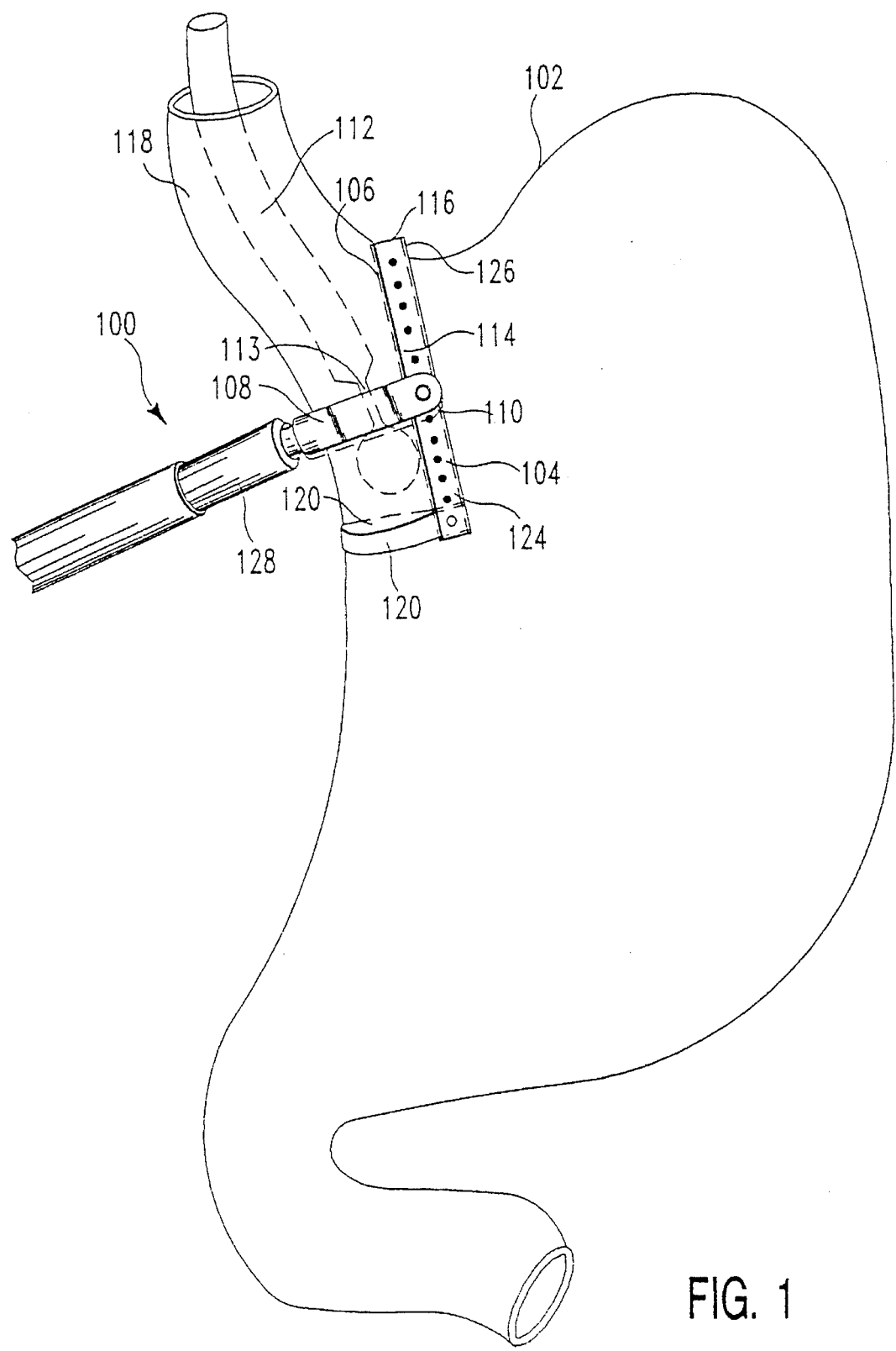
FIG. 1 is a side elevation schematic of a stomach having the present vertically banded gastroplasty device in position, still held by the leading end of the laparoscopic instrument of the present invention.

In accordance with the present invention, an apparatus and method which enable vertical banded gastroplasty (VBG) to be performed without the use of staples are disclosed. Further in accordance with the present invention, a laparoscopic instrument capable of rotating surgically functional elements attached to the instrument is disclosed. The laparoscopic instrument is capable of rotating surgically functional elements at least 90 degrees, and preferably at least 180 degrees, in a plane which is relatively parallel to a horizontal plane passing through the longitudinal centerline of a lever arm attached to the surgically functional elements. Further, use of this laparoscopic instrument in combination with the apparatus and method which permits VBG without the use of staples is described.

Since the surgically functional VBG elements of the present invention were originally developed for use in laparoscopic surgery, the detailed description which follows is in terms of this method of surgery. However, as is readily apparent, the method and apparatus which enable vertical banded gastroplasty to be performed without using staples are equally applicable for VBG performed using the more standard open surgery techniques.

The laparoscopic surgical procedure for VBG is as follows. The patient is prepared in standard fashion, as if they were to undergo the open surgery procedure for vertically banded gastroplasty (VBG). A gastroscope for inspecting the inner surface of the stomach is placed into the stomach through the patient's mouth. Typically three laparoscopic ports are placed, using procedures well known in the art, after which a pneumoperitoneum to expand the peritoneal cavity is achieved, also using standard technique. The three port locations are as follows: Two ports are placed in the right upper quadrant, one port below the costal margin in the midclavicular line; a second port slightly inferior to the first; and a third port above the umbilicus, used for a second endoscope (to permit viewing of the stomach exterior). The size of the ports ranges from about 5 mm to about 35 mm in diameter, depending on the instrument which is inserted through the port.

The stomach is grasped through the port located in the right upper quadrant (or may be grasped through an additional port located in the left upper quadrant), using a technique known in the art, such as with an atraumatic forceps, and is then pulled to one side (typically the left) where it is held by an assistant. The primary surgeon then divides the lesser omentum, including the hepato-esophageal ligament, thus providing access to the lesser sac. Division of the lesser omentum can be accomplished with an Endo-GIA® type stapler, available from U.S. Surgical Corp., or using clips or ties. Care must be taken not to damage the nerves of laterjet or gastric arteries. A tubular portion of the laparoscopic VBG instrument which contains the surgically functional elements of the instrument is then placed into the abdomen through one of the upper quadrant ports. The laparoscopic VBG instrument is then opened inside the abdomen, so that the surgically functional elements of the instrument are extended and carefully positioned. The present invention employs the use of clamping bars to form the upper gastric pouch. These clamping bars are positioned so that a first clamping bar is anterior and a second clamping bar lies posterior to the stomach exterior. Optionally, during the entire period of laparoscopic VBG instrument manipulation within the abdomen, a gastroscope may be used in the stomach to help identify structures as well as to empty and manipulate the stomach.

After the VBG clamping bars are properly positioned, the gastroscope is withdrawn and a Maloney dilator of the appropriate size is inserted transorally into the stomach. This step insures that the pouch to be created upon engagement of the clamping bars will be of the appropriate size. Once exact positioning has been accomplished, the inside edges of the clamping bars will be adjacent to the Maloney dilator and the upper ends of the clamping bars will be at the junction of the esophagus with the stomach. Once the position of the clamping bars has been confirmed, the clamping bars are engaged to form the upper gastric pouch. The clamping bars are then released (separated) from the remaining portion of the surgically functional elements, and these elements are moved clear of the stomach and retracted into the tubular portion of the laparoscopic instrument. The laparoscopic instrument is then removed from the abdomen and the stomach is inspected. The stomach exterior is inspected through the umbilicus endoscope. If needed, the gastroscope can be reintroduced into the interior of stomach 102 to confirm adequate hemostasis and adequate pouch formation. Once the VBG has been completed and inspected, the remaining instruments are removed, the port sites are inspected as the ports are withdrawn, and the incisions are sutured closed.

FIG. 1 shows the laparoscopic instrument 100 for performing VBG in position relative to a stomach 102. Upper gastric pouch first clamping bar 104 lies under first clamping bar holder 124 which is attached to first jaw structure 108. Pouch first clamping bar 104 is positioned anterior to stomach 102. Pouch second clamping bar 106 (shown in shadow form) lies under second holder 126 (shown in shadow form) which is attached to second jaw structure 110 (shown in shadow form) and is positioned posterior to stomach 102. Presence of the Maloney dilator 112 assures that the pouch created will be of the appropriate size. The Maloney dilator 112 shown in FIG. 1 has been particularly modified for use in combination with the present laparoscopic instrument. Typically the Maloney dilator does not "neck down" as shown in FIG. 1. The constricted area 113 of modified Maloney dilator 112 serves as an indicator of the desired placement position for jaw structures 108 and 110. When exact positioning has been accomplished, the inside edge 114 of pouch first clamping bar 104 is adjacent Maloney dilator 112 and the upper end 116 of first clamping bar 104 is at the junction of esophagus 118 with stomach 102. The separable portion of VBG instrument 100, which remains in the body after the procedure, preferably includes clamping bars 104 and 106 and a band 120 which is attached to clamping bars 104 and 106. Once the desired positioning has been obtained, the spacing between first clamping bar 104 and second clamping bar 106 is closed by manipulating instrument 100, to form the desired upper gastric pouch; with band 120 simultaneously forming a restricted opening at the bottom of this pouch. Once the upper gastric pouch is properly formed, the separable portion of VBG instrument 100 is separated by releasing clamping bars 104 and 106 from their holders 124 and 126, respectively. First clamping bar holder 124 is then rotated so that it is parallel with first jaw 108, while second clamping bar holder 126 is rotated so that it is parallel with second jaw 110. Jaw structures 108 and 110 are opened, and moved away from stomach 102. Once jaw structures 108 and 110 are clear of stomach 102, jaw structures 108 and 110 are then closed, and tubular section 128 of laparoscopic instrument 100 is advanced for removal from the insertion port (not shown).

Figure 2:
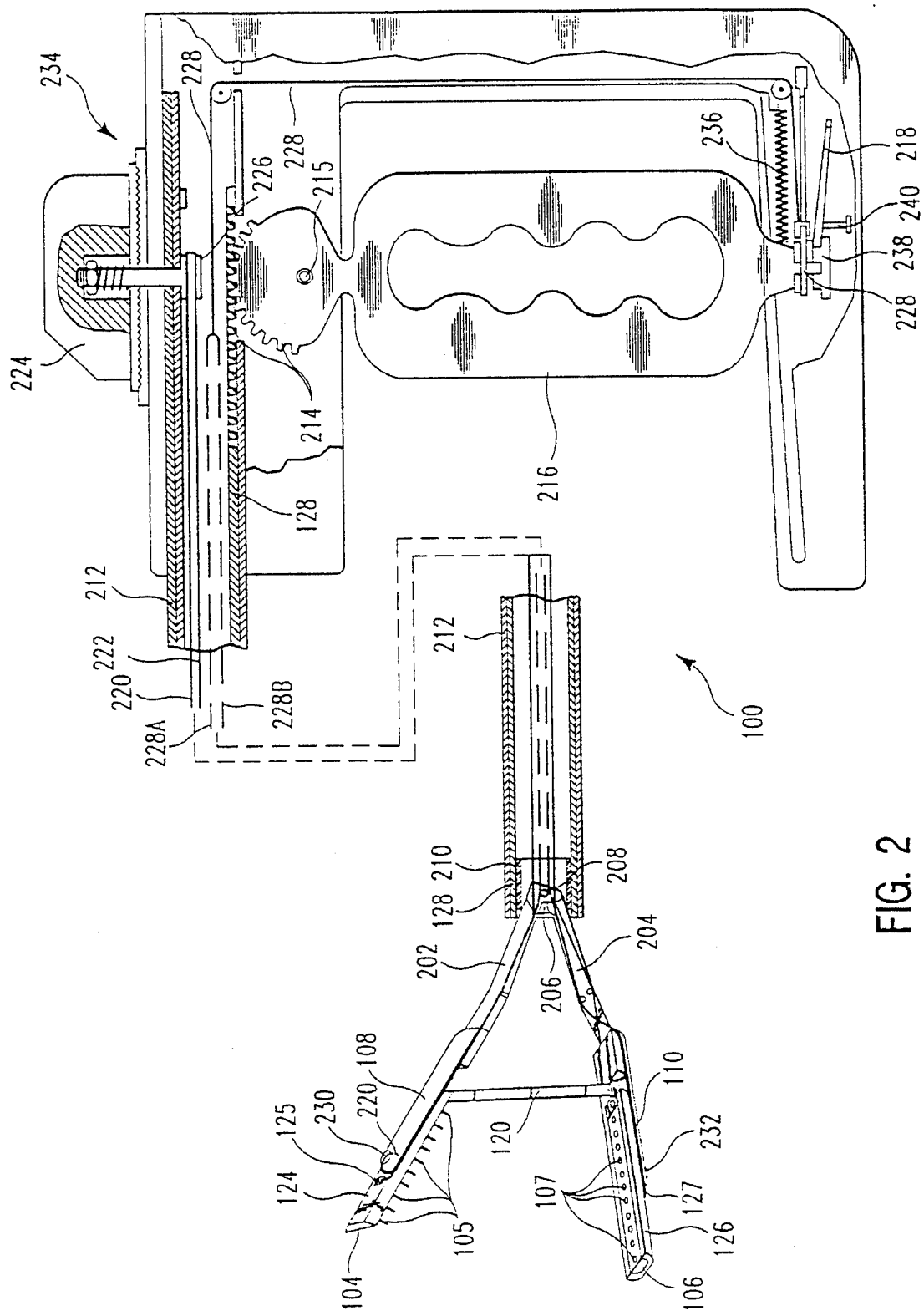
FIG. 2 is a side elevation schematic, partly in section, showing a laparoscopic instrument, with the jaws of the instrument in the open position, and with the stomach clamping bars and attached banding strip in place within the jaws.

FIG. 2 is a side elevation schematic, with break-away illustration, of laparoscopic instrument 100, including the VBG surgically functional elements. The VBG surgically functional elements include first clamping bar 104 having piercing pins 105, second clamping bar 106 having pin-receiving openings 107, and banding strip 120 attached to clamping bars 104 and 106. First clamping bar 104 is attached to first clamping bar holder 124 which is attached to a first jaw 108 of laparoscopic instrument 100 via a first pivot means 230. Second clamping bar 106 is attached to second clamping bar holder 126 which is attached to a second jaw 110 of laparoscopic instrument 100 via a second pivot means 232. Clamping bars 104 and 106 can be rotated at least 180 degrees around pivot means 230 and 232 by means of cables 220 and 222, respectively. Cables 220 and 222 are connected to double pulley 226, which is attached to dial 224. The setting on dial 224 preferably has a 1:1 relationship with the amount of rotation of clamping bar holders 124 and 126. Thus, when the dial is at a setting of 0 degrees, clamping bar holders 124 and 126 are parallel with jaws 108 and 110, respectively. When dial 224 is rotated 20 degrees in a clockwise direction, both clamping bar holders 124 and 126 are rotated 20 degrees in a clockwise direction (so they are lined up for engagement with each other). Lever arms 202 and 204 which are attached to jaws 108 and 110, respectively, joined at pivot 208 which is held in position relative to the longitudinal centerline of first tubular structure 128 by a hollow tubular insert 210 which sets inside tubular structure 128. The pin of pivot 208 passes through at least a portion of the wall of hollow tubular insert 210. Hollow insert 210 fits snugly against the inside of tubular structure 128, and slides within tubular structure 128 as it advances from and retracts into second tubular structure 212. Insert 210 is hollow, to permit cables 220, 222 and 228 to pass through first tubular structure 128. First tubular structure 128 is used to contain lever arms 202 and 204 and the surgically functional elements attached thereto during the actual procedure when the instrument leading end is inserted into the port entering the patient. Thus, all of the elements shown in FIG. 2 forward of pivot 208 must be acted upon by motion of the of first tubular structure 128 as the surgeon's needs dictate. To accomplish this, first tubular structure 128 is capable of extending from and retracting into second tubular structure 212 which is attached to handle 234. Spring 206 which operates to apply force to lever arms 202 and 204 causes an increase in the included angle between (opening of) these lever arms when first tubular structure 128 is retracted. As first tubular structure 128 is extended, it overcomes the force applied by spring 206 and causes the included angle between lever arms 202 and 204 to be reduced. At full extension of first tubular structure 128, lever arms 202 and 204 are closed but not in contact with each other and they, as well as the surgically functional elements attached to them, are at least partially enclosed within first tubular structure 128. To enable first tubular structure 128 to be extended from and retracted into second tubular structure 212, first tubular structure 128 is connected to an actuating means such as gear means 214. As hand grip 216 of handle 234 is pushed forward, toward the tubular portions of laparoscopic instrument 100, the upper portion of grip handle 216, gear means 214, travels toward the trailing, rear portion of handle 234 due to the pivoting action at pivot 215. This action of gear means 214 acts to retract first tubular structure 128. As hand grip 216 of handle 234 is pulled backward, toward the trailing end of handle 234, gear means 214 swings forward, extending first tubular structure 128. Thus, the position of hand grip 216 is backward at the time the surgeon inserts laparoscopic instrument 100 into the patient's port opening. Once the insertion is completed, and the surgeon wants to use the surgically functional elements, hand grip 216 is pushed forward toward the tubular portion of laparoscopic instrument 100, to retract first tubular section 128 and make the surgically functional elements available for use.

Once clamping bars 104 and 106 are in the desired position and the surgeon wants to engage the clamping bars to form the pouch, he pulls hand grip 216 backward to close lever arms 202 and 204 and thereby engage clamping bars 104 and 106. The surgeon is now ready to release clamping bars 104 and 106 from clamping bar holders 124 and 126, respectively. To accomplish this, the surgeon pulls hand grip 216 to the maximum backward travel, pulling cable 228 and releasing a mechanism 125 and 127 (not shown) on clamping bar holders 124 and 126, respectively, so that clamping bars 104 and 106 are released from holders 124 and 126, respectively. Hand grip 216 is held forward from its backward most position by spring 236 to prevent release of clamping bars 104 and 106 until the surgeon is ready for their release.

As previously described, it is preferable to have a safety means to prevent potential damage to the patient's stomach which could occur if the surgeon became momentarily distracted for some reason and attempted to withdraw laparoscopic instrument 100 without releasing engaged clamping bars 104 and 106. Lever 218 at the base of handle 234 is moved into place against extension 238 of hand grip 216 by spring 240 at the time hand grip 216 is moved forward to close levers 202 and 204 and engage clamping bars 104 and 106. Lever 218 prevents the surgeon from moving hand grip 216 backward in an attempt to open levers 202 and 204 until the surgeon has moved hand grip 216 all the way forward, releasing engaged clamping bars 104 and 106.

Figure 3:
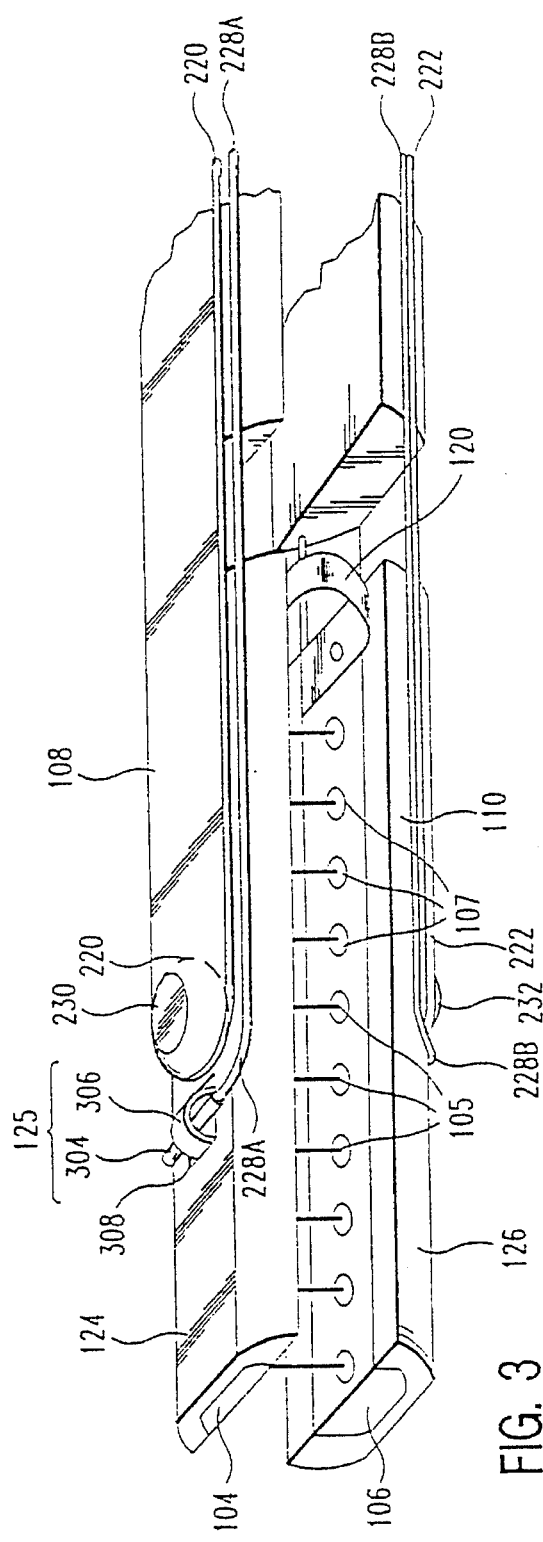
FIG. 3 is a more derailed schematic of one preferred embodiment of the clamping apparatus used to perform VBG without the use of staples. In addition, the means for releasing the clamping bars of this apparatus from the clamping bar holders is shown in detail. Also shown in more detail are the jaws of the laparoscopic instrument, including the pulley means for rotating a surgically functional element within a plane which is substantially parallel to a plane extending horizontally through the longitudinal centerline of the laparoscopic instrument jaw.
Figure 3A:
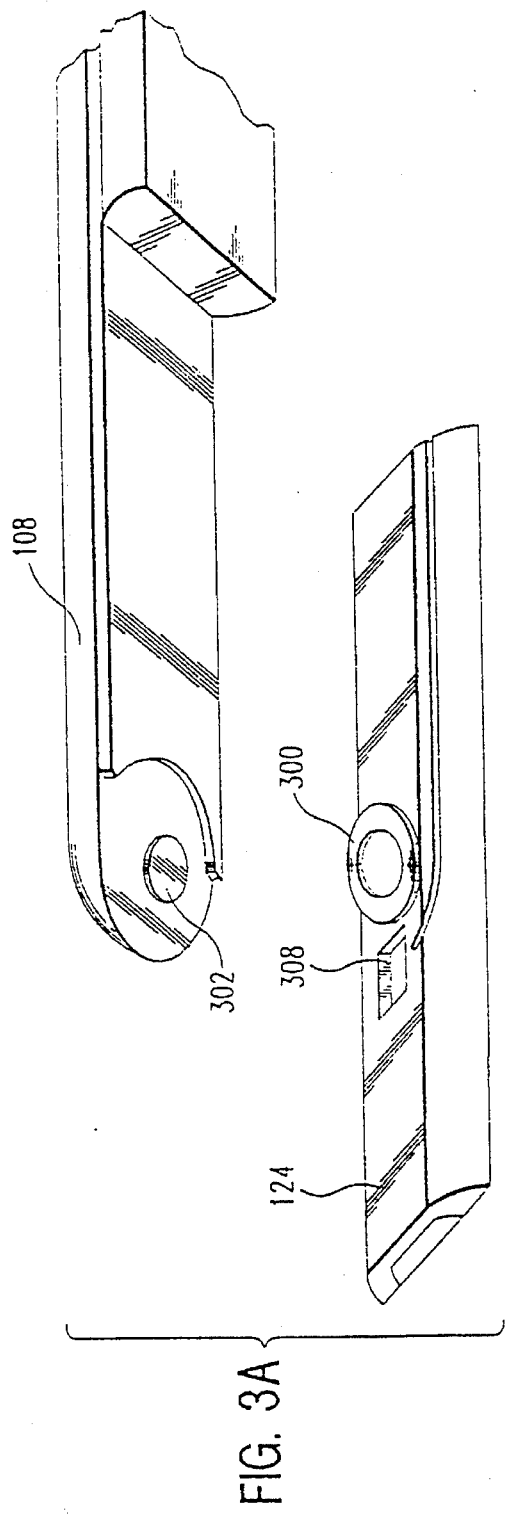
FIG. 3A is a more detailed schematic of one preferred embodiment of the clamping apparatus shown in FIG. 3.

FIG. 3 is a more detailed illustration of the clamping apparatus used to perform VBG without the use of staples. In addition, FIG. 3 shows in more detail one preferred means, of the kind shown in FIG. 2, for releasing the clamping bars from a laparoscopic instrument 100. Also shown in more detail are jaws 108 and 110 of laparoscopic instrument 100, including the pulley means for rotating a surgically functional element at least 180 degrees within a plane which is substantially parallel to a plane extending horizontally through the longitudinal centerline between laparoscopic instrument jaws (108 and 110).

The apparatus for performing VBG without the use of staples comprises clamping bar 104, clamping bar 106 and banding strap 120. Although this apparatus is shown in FIG. 3 attached to clamping bar holders 124 and 126, respectively, of laparoscopic instrument 100 jaws 108 and 110, respectively, it is readily apparent that this apparatus can be used in open surgery and clamped into engaged position using any compatible means of applying engagement leverage to clamping bars 104 and 106.

When the apparatus for performing VBG without staples is used in combination with a laparoscopic instrument, it is necessary to be able to position the apparatus as desired relative to the stomach without the accessibility available during open surgery. In addition, as mentioned above, it would be advantageous to be able to reform the vertical gastroplasty without the need for a circular hole and staple lines in the stomach. To accomplish this purpose, the laparoscopic instrument of the present invention has the capability of rotating clamping bar holders 124 and 126 relative to laparoscopic instrument 100 jaws 108 and 110. Holders 124 and 126 can each be rotated at least 180 degrees, in a plane substantially parallel to a plane passing horizontally through the longitudinal centerline of jaws 108 and 110, respectively. To accomplish this, a rotational means such as the pulley means shown in FIG. 3 can be used. Pulley 300, attached to the surface of clamping bar holder 124 fits over pivot 302 attached to jaw 108; cable 220 which moves on pulley 226 in response to the turning of dial 224 also moves on pulley 300, so that as dial 224 is turned, clamping bar holder 124 rotates.

Further, once the clamping apparatus has been positioned and engaged to form the upper gastric pouch, it is necessary to release the clamping apparatus from the laparoscopic instrument. FIG. 3 shows a preferred means, of the kind shown in FIG. 2 at 125 and 127, for separating the clamping device from a laparoscopic instrument 100. Separating means 125 is comprised of strap 306 attached to the upper surface of clamping bar 104. Strap 306 is positioned to pass through opening 308 in clamping bar holder 124. A pin, 304, is placed through strap 306, to hold clamping bar 104 in position against clamping bar holder 124. Pin 304 is attached to cable 228 which is manipulated using laparoscopic instrument 100 handle 234, as previously described. By pulling handle grip 216 all the way backward in handle 234, cable 228 is pulled farther into handle 234, causing pin 304 to be pulled out of retaining strap 306, so that clamping bar 104 is released from its holder 124. As is apparent looking at FIG. 3, pin 304 cannot be removed when clamping bar 124 is parallel to jaw 108 and cable 228 is at a right angle to pin 304. It is only after clamping bar 124 has been rotated into position over the stomach, as shown in FIG. 1, that cable 228 will be in a straight line with pin 304 so that pin 304 can be removed, releasing clamping bar 124.

Figure 4:
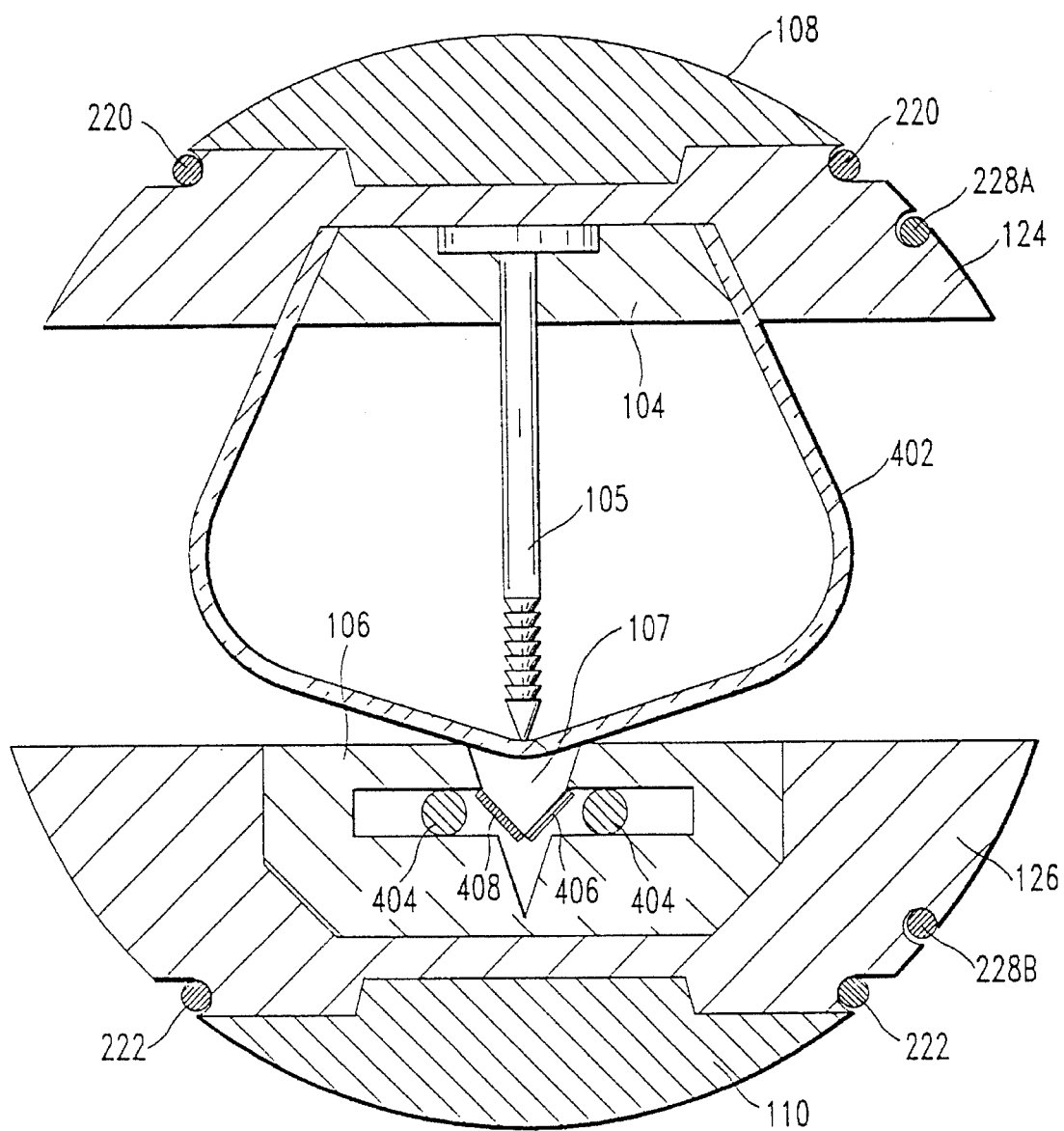
FIG. 4 is a more detailed schematic of a preferred clamping bar locking mechanism which is activated upon engagement of the clamping bars illustrated in FIG. 3.

FIG. 4 shows a more detailed illustration of a preferred clamping bar locking mechanism which is activated upon engagement of clamping bars of the kind illustrated in FIG. 3. Clamping bar 104 includes piercing pins 105 which are engaged with clamping bar 106 via openings 107 in clamping bar 106. Piercing pins 105 are typically covered by a protective material such as sheath 402 prior to engagement of clamping bars 104 and 106. Sheath 402 prevents piercing pins 105 from scraping or piercing tissue during the surgical steps for positioning the clamping apparatus. Sheath 402 can be made of any material which can be pierced by piercing pins 105 under the available clamp engagement leverage and which is compatible with the patient's internal bodily functions in general. Typically, sheath 402 is constructed from Silastic® (polyglycolic acid). Preferably, sheath 402 is constructed from cat gut or a similar material which is dissolved and assimilated harmlessly into the body. Piercing pins 105 can be constructed from any non-corrosive, non-degradable, non-absorbable, rigid material having adequate mechanical properties; typically piercing pins 105 are constructed from stainless steel, vanadium steel, titanium, or combinations thereof. Clamping bars 104 can be constructed from a non-corrosive, non-absorbable metal, a non-degradable, non-absorbable plastic, or from combinations thereof. Non-corrosive, non-degradable and non-absorbable pertain to the conditions of use, that is when contacted with body parts and fluids to which the clamping bars and piercing pins will be exposed.

Once engagement leverage is applied, by the closing of jaws 108 and 110 (not shown) of laparoscopic instrument 100, piercing pin 105 enters opening 107 and passes through a retaining membrane or surface. A preferred embodiment of a retaining surface is shown in FIG. 4 in the form of flat wires 406 and 408. These flat wires are positioned at an oblique angle to each other in the direction of entry of piercing pin 105, whereby piercing pin 105 is prevented from subsequently exiting opening 107 by the presence of flat wires 406 and 408. Flat wires 406 and 408 are held into position by contoured retaining spring 404. The advantage to this arrangement is that contoured retaining spring 404 can be removed should it be desired to provide a relatively easy exit of piercing pins 105 from openings 107. This makes it possible to release the engagement of clamping bars 104 and 106 by a single step, the movement of contoured retaining spring 404 to a position so that it no longer holds flat wires 406 and 408 against the exit of piercing pins 105 from openings 107.

Figure 5:
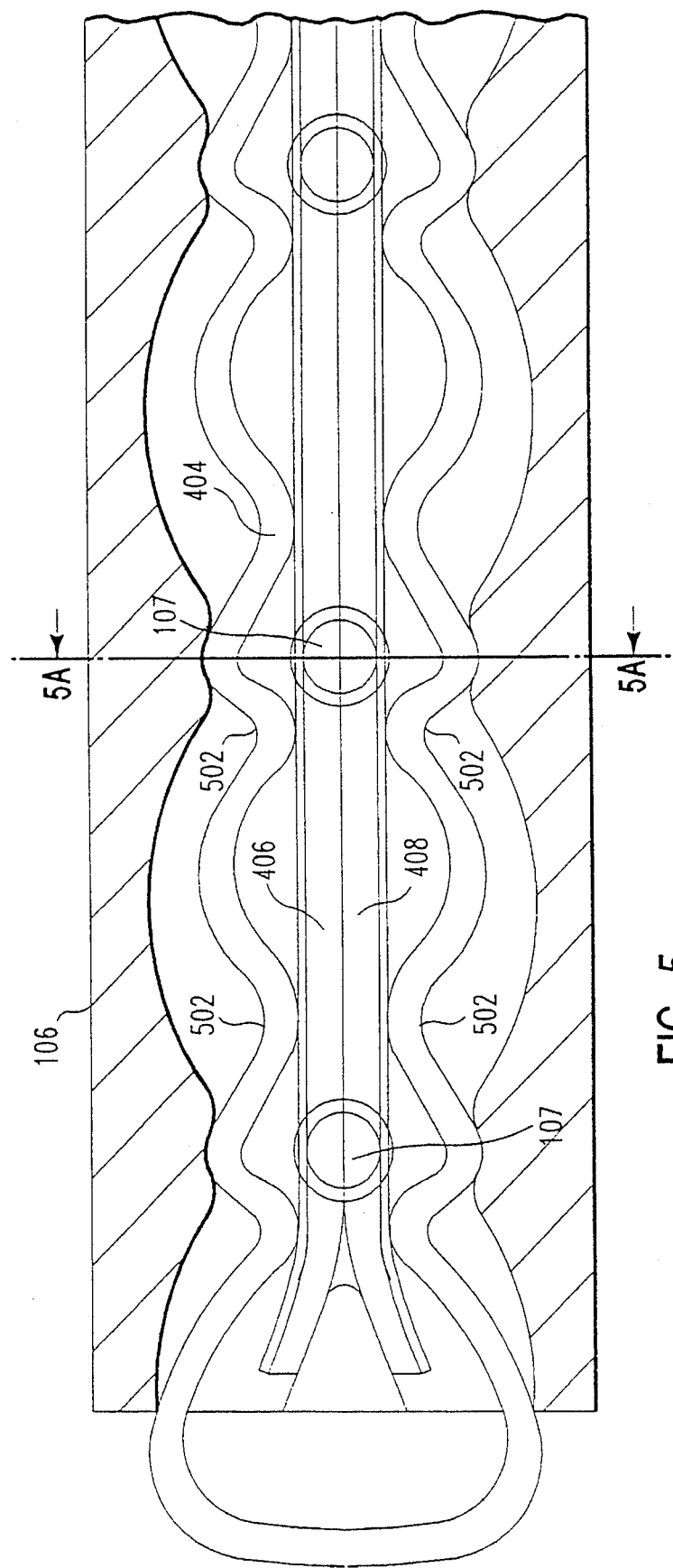
FIG. 5 illustrates a preferred release means for use in combination with the locking mechanism shown in FIG. 4. This release means makes it relatively easy to remove the clamping bars and reverse the VBG should this become necessary.
Figure 5A:
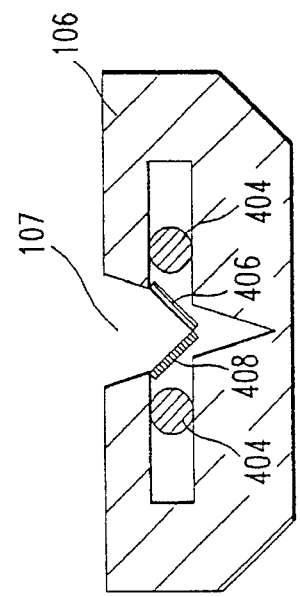
FIG. 5A is a cross-sectional view taken along lines 5A—5A of FIG. 5.

FIG. 5 illustrates in more detail the preferred release means for use in combination with the locking mechanism shown in FIG. 4. This release means makes it relatively easy to remove the clamping bars and reverse the VBG should this become necessary. Contoured retaining spring 404 is held in place against flat wires 406 and 408 by a contoured shape within clamping bar 124 which is designed to work in cooperation with the shape of contoured retaining spring 404. By moving contoured spring 404 either forward or backward, the pressure exerted at positions 502 (over the length of the clamping bar) against flat wires 406 and 408 is removed and flat wires 406 and 408 are free to lie flat within opening 107. This makes it possible to remove piercing pins 105 from opening 107.

FIG. 6 shows a second preferred embodiment clamping bar locking mechanism. The upper portion of the clamping mechanism, shown in FIG. 6A, is essentially the same as the upper portion of the clamping mechanism shown in FIG. 4. The lower portion of the clamping mechanism, shown in FIG. 6B and 6C is believed to offer advantages over the lower clamping mechanism shown in FIG. 4.

Once engagement leverage is applied to the jaws 108 and 110 (not shown) of laparoscopic instrument 100, piercing pin 105 enters opening 607 of clamping bar 606 and passes through retaining surface 608 at slotted opening 609. Retaining surface 608 optionally, but preferably, exhibits a bent leg 612 adjacent narrow slotted opening 609. Bent leg 612 makes it easier for piercing pin 105 to pass through slotted opening 609 and more difficult for piercing pin 105 to exit once having entered slotted opening 609. typically bent leg 612 of retaining surface 608 is bent such that an angle, or, typically ranging from about 120 degrees to about 140 degrees, is formed between the straight portion and bent leg 612 of retaining surface 608.

Once piercing pin 105 has entered slotted opening 609, it is held in place by ridges 601 on piercing pin 105 and optionally by bent leg 612.

With reference to FIG. 6C, should it be desirable to reverse the vertically banded gastroplasty in a subsequent procedure, the surgeon inserts a hook (not shown) into opening 610 on the leading end of retaining surface 608 and pulls so that the enlarged end 611 of slot 609 lines up under opening 607 of clamping bar 606. Piercing pin 105 is then easily removed from retaining surface 608.

Figure 7:
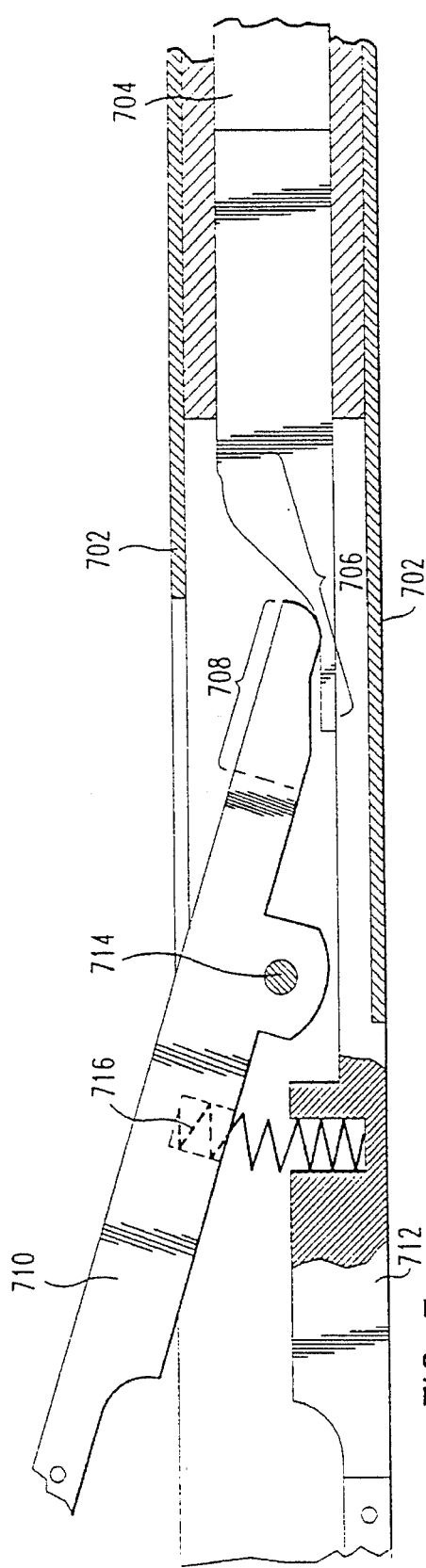
FIG. 7 is a schematic showing in detail the mechanism used to open and close the lever arms of the laparoscopic instrument when a ramped push rod is used to open and close the lever arms.
Figure 7A:
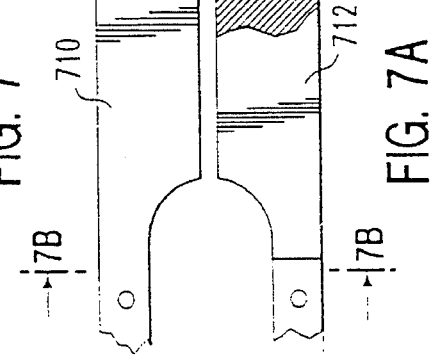
FIG. 7A is a schematic view of the device shown in FIG. 7, showing the clamping jaw in a closed position.
Figure 7B:
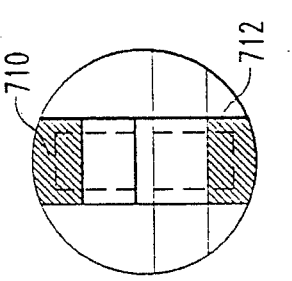
FIG. 7B is a cross-sectional view taken along lines 7B—7B of FIG. 7A.

FIG. 7 shows a second preferred embodiment of a means for opening and closing the jaws of laparoscopic instrument 100. A tubular member 702 which is attached to a handle (not shown) supports push/pull rod 704 having a ramp 706 on its leading end. Ramp 706 operates in conjunction with a second ramp 708 located on the trailing end of upper jaw 710. Lower jaw 712 can be movable, but is typically rigid and attached to tubular member 702. Upper jaw 710 operates on pivot 714 which is attached to tubular member 702 to anchor upper jaw 710 at approximately the cross-sectional horizontal centerline of tubular member 702.

A force applying means such as spring 716 is used to maintain jaws 710 and 712 in a normally-open position (having an included angle). To close jaws 710 and 712, push/pull rod 704 is pushed forward so that ramp 706 slides under ramp 708, causing upper jaw 710 to close.

Figure 8:
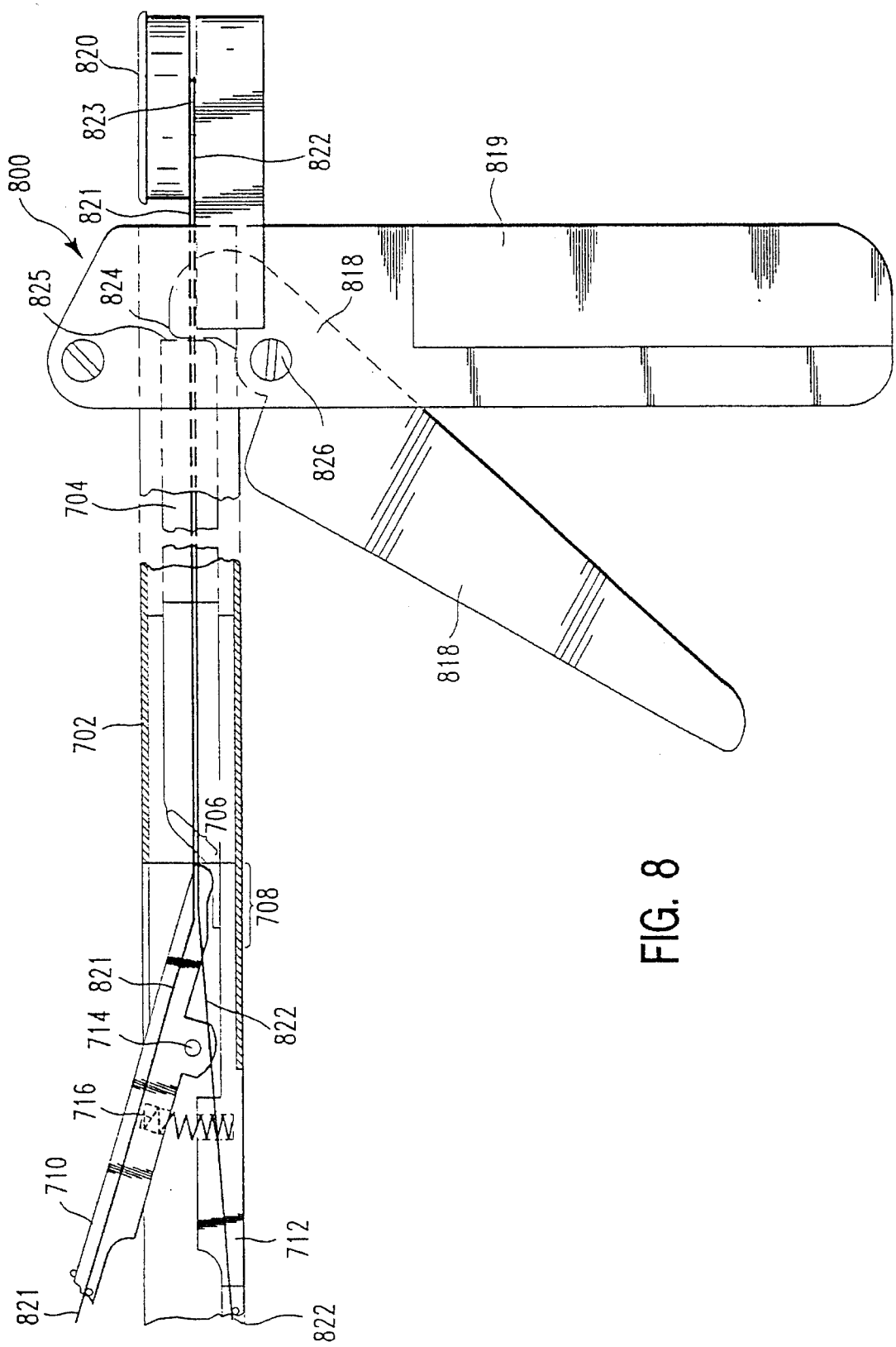
FIG. 8 is a schematic showing a second embodiment of a handle which can be used to support and control operation of the laparoscopic instrument.

FIG. 8 shows a schematic of the second preferred means (FIG. 7) of opening and closing the jaws of the laparoscopic instrument, as related to a handle 800 from which the instrument can be operated by a surgeon. As previously described, upper jaw 710 and lower jaw 712 are maintained in a normally-open position by spring 716. To close jaws 710 and 712, push/pull rod 714 must be moved forward. Handle 800 includes lever 818 having end 824 in contact with push/pull rod 704 at its trailing edge 825. Lever 818 is attached to grip member 819 of handle 800 via pivot 826. By pulling lever 818 toward grip member 819, end 824 of lever 818 pushes against trailing edge 825 of push/pull rod 704, causing push/pull rod 704 to move forward; ramp 706 at the leading end of push/pull rod 704 operates in conjunction with ramp 708 at the trailing end of jaw 710 to close jaws 710 and 712.

Dial 820 is used to control the position of surgically functional elements (not shown) at the leading end of the instrument (not shown). Cables 821 and 823, attached to double pulley 823 are used to direct functional elements attached to the leading end of jaws 710 and 712, respectively, in the manner previously described herein.

The preferred embodiments of the present invention, as described above and shown in the FIGS. are not intended to limit the scope of the present invention, as they are merely intended to illustrate the concepts of the invention. The scope of the invention is demonstrated by the claims which follow, since one skilled in the art can, with minimal experimentation, extend the scope of the embodiments to match that of the claims.

What is claimed is:

1. An apparatus for use in vertical banded gastroplasty comprising:

a clamping structure comprising first and second relatively pivotable clamping bars connected to a handle, said clamping bars being engagable in combination with stomach walls and externally of said walls to form an upper gastric pouch, said clamping bars engaging upon the application of force to said handle;

said first clamping bar comprising piercing pins capable of engaging pin-receiving openings in a second clamping bar;

said pin-receiving openings comprising a retaining membrane or a retaining surface mechanism which acts to prevent said piercing pins from exiting said pin-receiving openings after engagement of said first and said second clamping bars.

2. The apparatus of claim 1, wherein said retaining surface is comprised of a slotted surface, wherein each pin-receiving opening comprises a slot.

3. The apparatus of claim 2, wherein said slots include an enlarged opening at one end of each slot, whereby it is possible to release said piercing pin from said slot by moving said slotted surface relative to said pin-receiving openings so that said piercing pin is aligned directly with said enlarged opening of said slot.

4. An apparatus for use in vertical banded gastroplasty comprising:

a clamping structure comprising first and second clamping bars which can be engaged in combination with stomach walls to form an upper gastric pouch;

said first clamping bar comprising piercing pins capable of engaging pin-receiving openings in said second clamping bar;

said pin-receiving openings comprising a retaining membrane or a retaining surface mechanism that acts to prevent said piercing pins from exiting said pin-receiving openings after engagement of said first and said second clamping bars;

said retaining surface being comprised of at least two flat wires held at an oblique angle to the entry of said piercing pins into said pin-receiving openings.

5. The apparatus of claim 4, wherein said flat wires are held in position by a contoured retaining spring.

6. The apparatus of claim 5, wherein said contoured retaining spring can be adjusted to release the force exerted on said flat wires, whereby said piercing pins can be removed from said pin-receiving openings.

7. An apparatus for use in vertical banded gastroplasty comprising:

a clamping structure comprising first and second relatively pivotable clamping bars connected to a handle, said clamping bars being pivotable about a pivot axis and being engagable in combination with stomach walls and externally of said walls to form an upper gastric pouch, said clamping bars engaging upon the application of force to said handle;

said first clamping bar comprising piercing pins capable of engaging pin-receiving openings in a second clamping bar; and a band connecting said clamping bars at one end, said band being sized and connected to said clamping bars such that it provides a circumferential restraint for the gastric pouch when said clamping bars are engaged, said circumferential restraint defining a plane that is parallel to said pivot axis.

8. The apparatus of claim 7, wherein said piercing pins are constructed from material selected from the group consisting of stainless steel, vanadium steel, titanium and combinations thereof.

9. The apparatus of claim 7, wherein the portion of said clamping structure which provides basic supporting structure and is in contact with the exterior of said stomach wall is constructed from a material selected from the group consisting of a non-corrosive, non-absorbable metal, a non-degradable, non-absorbable plastic, and combinations thereof.

10. The apparatus of claim 7, wherein each of said bars has a trailing end and a leading end and a band connects said leading ends of said clamping bars.

11. An apparatus for use in vertical banded gastroplasty comprising:

a clamping structure comprising first and second relatively pivotable clamping bars connected to a handle, said clamping bars being engagable in combination with stomach walls and externally of said walls to form an upper gastric pouch, said clamping bars engaging upon the application of force to said handle;

said first clamping bar comprising piercing pins capable of engaging pin-receiving openings in a second clamping bar;

said piercing pins being covered at least in part by a protective material, said protective material having a resistance to piercing that is greater than that of tissue but less than the force required to cause said piercing pins to engage said pin-receiving openings, such that said piercing pins are prevented from piercing tissue prior to engagement with said pin-receiving openings.

12. The apparatus of claim 11, wherein said protective material is one capable of being dissolved and assimilated harmlessly into the body.

13. The apparatus of claim 10, wherein said protective material is selected from the group consisting of cat gut, polyglycolic acid and Silastic®.

14. A laparoscopic instrument for performing surgical functions, comprising the following elements:

a) at least one arm having a leading end and a trailing end;

b) a rotatable holder attached to said at least one arm at said leading end of said arm; and c) at least one surgically functional element attached to said rotatable holder said surgically functional element being attached to said holder prior to and during performance of the surgical function and released from said holder upon completion of the surgical function;

said rotatable holder being attached to said arm at a location along the surface of said rotatable holder which provides an essentially balanced moment of inertia of said rotatable holder about an axis normal to the surface at which said attachment occurs, and further including means affixed to said rotatable holder for rotating said rotatable holder;

said surgically functional element comprising a clamping bar and said rotatable holder being capable of rotating at least 180 degrees in a plane which is relatively parallel to a plane passing horizontally through the longitudinal center line of said arm to which said rotational holder is attached.

15. The laparoscopic instrument of claim 14, wherein said rotatable holder is capable of rotating at least 270 degrees.

16. A laparoscopic instrument for performing surgical functions, comprising the following elements:

a) at least one arm having a leading end and a trailing end;

b) a rotatable holder attached to said at least one arm at said leading end of said arm, said rotatable holder being attached to said arm at a location along the surface of said rotatable holder which provides an essentially balanced moment of inertia of said rotatable holder about an axis normal to the surface at which said attachment occurs, and said rotatable holder being capable of rotating at least 180 degrees in a plane which is relatively parallel to a plane passing horizontally through the longitudinal center line of said arm to which said rotational holder is attached;

(c) at least one surgically functional element attached to said rotatable holder; and (d) means affixed to said rotatable holder for rotating said rotatable holder;

(e) first and second lever arms joined by a pivot, and having a force applying means which acts in conjunction with said lever arms to apply pressure upon said levers, whereby said levers may be opened and closed; said lever arms attached to and working in combination with at least one tubular structure, wherein at least a portion of said tubular structure is attached to a handle that includes means for operating said force applying means, said handle also comprising a means for causing the rotation of said rotational holder, which rotational holder is attached at a leading end of at least one of said lever arms.

17. A method of using the laparoscopic instrument of claim 16 in combination with the apparatus of claim 1, comprising the steps of:

a) inserting said pouch-forming clamps mounted on said rotatable clamp holders, through a pre-prepared port into the abdominal cavity of a patient;

b) rotating said clamp holders so that said pouch-forming clamps are positioned with at least one clamp on the exterior, anterior side of the stomach and at least one clamp on the exterior, posterior side of the stomach;

c) engaging the pouch-forming clamps so they cooperate to form a secondary gastric pouch;

d) releasing said pouch-forming clamps from their clamp holders;

e) rotating said clamp holders so they are parallel with said lever arms;

f) removing the portion of said laparoscopic instrument other than said clamping apparatus from said abdominal cavity of said patient, through said pre-prepared port.

18. The method of claim 17, including an additional step preceding step a), of:

$a_2$) attaching a pouch-forming clamp to a rotatable clamp holder of a laparoscopic instrument.

* * * * *